United States Patent
Lovejoy et al.

[11] Patent Number: 6,031,454
[45] Date of Patent: Feb. 29, 2000

[54] WORKER-SPECIFIC EXPOSURE MONITOR AND METHOD FOR SURVEILLANCE OF WORKERS

[75] Inventors: Michael L. Lovejoy, Albuquerque, N.Mex.; John P. Peeters, Bethesda, Md.; A. Wayne Johnson, Albuquerque, N.Mex.

[73] Assignee: Sandia Corporation, Albuquerque, N.Mex.

[21] Appl. No.: 08/969,258

[22] Filed: Nov. 13, 1997

[51] Int. Cl.[7] .............................. G08B 1/08; G08B 23/00
[52] U.S. Cl. ................... 340/539; 340/691.1; 340/693.1; 340/693.5; 340/693.6; 340/573.1; 340/632; 340/521; 340/825.36; 340/825.49; 250/388; 250/484.5
[58] Field of Search ..................................... 340/539, 691, 340/573, 693, 825.36, 825.49, 691.1, 691.4, 693.1, 693.5, 693.6, 573.1, 632, 521; 250/336.1, 337, 472.1, 374, 388, 484.5; 73/23.2

[56] References Cited

U.S. PATENT DOCUMENTS

| | | |
|---|---|---|
| 4,642,463 | 2/1987 | Thoms .................................. 250/336.1 |
| 5,099,127 | 3/1992 | Kitaguchi et al. .................. 250/370.07 |
| 5,132,543 | 7/1992 | Valentine et al. ........................ 250/388 |
| 5,173,609 | 12/1992 | Lacoste et al. ..................... 250/370.07 |
| 5,235,318 | 8/1993 | Schulz ...................................... 340/505 |
| 5,468,968 | 11/1995 | Bailey et al. ............................ 250/435 |
| 5,502,445 | 3/1996 | Dingwall et al. .......................... 342/51 |
| 5,552,772 | 9/1996 | Janky et al. .............................. 340/573 |
| 5,652,570 | 7/1997 | Lepkofker ................................ 340/573 |
| 5,731,757 | 3/1998 | Layson, Jr. ............................... 340/573 |

FOREIGN PATENT DOCUMENTS

1-45595  6/1989  Japan .

*Primary Examiner*—Donnie L. Crosland
*Attorney, Agent, or Firm*—Gregory A. Cone

[57] ABSTRACT

A person-specific monitor that provides sensor information regarding hazards to which the person is exposed and means to geolocate the person at the time of the exposure. The monitor also includes means to communicate with a remote base station. Information from the monitor can be downloaded at the base station for long term storage and analysis. The base station can also include means to recharge the monitor.

20 Claims, 5 Drawing Sheets

FIG. 7

WORKER-SPECIFIC EXPOSURE MONITOR AND METHOD FOR SURVEILLANCE OF WORKERS

STATEMENT REGARDING FEDERALLY SPONSORED RESEARCH OR DEVELOPMENT

This invention was made with Government support under Contract DE-AC04-94AL85000 awarded by the U.S. Department of Energy. The Government has certain rights in the invention.

CROSS REFERENCE TO RELATED APPLICATIONS

A related application is being filed concurrently herewith, entitled "Monitoring Personnel in Perilous Environments" to Michael L. Lovejoy, Michael B. Murphy, William P. Wiesmann, A. Wayne Johnson, and Stephen P. Bruttig, attorney docket no. SD-6048 which covers more specifically the radar-responsive tag disclosed herein, and the specification thereof is incorporated herein by reference in its entirety.

BACKGROUND OF THE INVENTION

This invention relates generally to methods and apparatus for monitoring occupational exposures of workers and, more specifically, to a worker-specific monitor which can be used to monitor for any type of exposure or combination of exposures and produce cumulative exposure records throughout the lifetime of the worker using the same device. The monitor can also be utilized as a timecard and, with minor modifications, serve as a highly sensitive security badge with both chemical and positional sensing capabilities.

The health effects of exposures to toxic elements in the workplace are increasingly a public concern. As a result of this concern, a number of different technologies have been developed to improve the monitoring of workers. In the case of radiation, a preferred option has been the use of personal monitors. With the miniaturization of electronics, the flexibility and ease of use of radiation monitors has been substantially improved in recent years offering capabilities such as on-the-fly readings of current and even cumulative exposures.

However workplace hazards are generally complex and, in fact, only rarely related to radiation. Despite this fact the market currently offers very little in terms of chemical monitors. Furthermore a major limitation of current monitors is that they are bulky and usually limited to a single or narrow group of hazards.

The patent literature reveals a number of references to various sensors designed to be worn or carried by individuals. U.S. Pat. No. 4,485,442 entitled CUMULATIVE EXPOSURE METERING SYSTEM describes a general timed cumulative exposure monitoring system. U.S. Pat. No. 4,642,463 entitled INTELLIGENT RADIATION MONITOR describes an intelligent radiation monitor with a convenient combined data download/recharge feature. U.S. Pat. No. 5,099,127 entitled PORTABLE INTENSITOMETER AND APPARATUS FOR CENTRALIZED CONTROL OF EXPOSURE USING THE INTENSITOMETER describes a portable intensitometer which allows cumulative radiation exposure monitoring over time. U.S. Pat. No. 5,173,609 entitled DEVICE FOR THE DETECTION OF RADIATION THAT ENDANGERS LIVING BEINGS describes a small credit-card type identification badge with cumulative radiation detection capability and a radio data transmission feature. U.S. Pat. No. 5,179,281 entitled EXTREMITY DOSIMETRY SYSTEM, DOSIMETER AND METHOD describes an extremity thermoluminescent dosimeter and housing system. U.S. Pat. No. 5,468,968 entitled AIR QUALITY MONITORING SYSTEM AND PROCESS describes an air quality monitoring system with a bar code identification system for individual workers. Japanese Pat. No. AU 1-145595 entitled INDIVIDUAL EXPOSURE MANAGING DEVICE describes a timecard combined with a radiation dose collection system. U.S. Pat. No. 5,502,445 entitled SYSTEM AND METHOD FOR REMOTE IDENTIFICATION OF CODED ARTICLES AND THE LIKE describes an electronic remote interrogation and identification system using a microwave beam.

None of these prior art patents discloses a monitor or security badge which combines in a highly compact unit an accurate positional capability which works within buildings with a capability to monitor for any type of chemical/physical exposure or combination of exposures. Similarly, none of these prior art patents discloses a genome-specific hazard monitor which can be tailored specifically to monitor the combination of hazards a given individual may be most sensitive to due to a genetic predisposition and/or prior occupational exposures.

SUMMARY OF THE INVENTION

This invention comprises a small monitor which can easily be adapted to monitor for any type of exposure or combination of exposures and allow for the monitoring of different types of cumulative occupational exposures over the lifetime of a worker using the same device. The monitor automatically updates the exposure records of each given worker in a database and also serves as a timecard. The monitor is designed in such a way that it can either be used in an industrial setting or be used for personal applications. For example, the monitor can easily be adapted to serve as a person-specific (or genomic) monitor, tailored specifically to allow individuals to self-monitor themselves for exposures to given chemicals or combination of hazards to which they may have a unique susceptibility (or genetic predisposition) as determined by medical and genetic tests. The monitor also includes an optional highly accurate positional capability for large industrial sites, buildings, or other places of limited vision, to allow exposures to be pinpointed to a given location and allow an overall exposure picture to be automatically drawn across an entire plant or factory. Conversely, the positional capability can notify the worker when he enters an exclusion or dangerous area. In addition, in case of an emergency, a worker can press an emergency call button on the monitor which allows the worker to be precisely located and allow for effective intervention. Finally the positional capability combined with an external chemical sensing capability (which can be specifically tailored for any type of chemical) allows this monitor to be used as a security badge for sensitive security jobs such as airplane maintenance crews or workers in nuclear facilities.

Since this monitor is meant to be small, simple to use, of low cost, universal, and can be tailored specifically to the exposure monitoring needs of each given individual over a period of many years, the implications of this technology is that worker monitoring could become much more proactive and allow across-the-board early intervention not only for individual workers but also for groups of workers. Thereby this technology could significantly help reduce the medical and legal consequences of occupational exposures.

A major concern with occupational exposures is that workers frequently change locations and tasks and therefore their exposure patterns vary frequently. Over a period of years the general nature of the hazards a worker might be exposed to is also likely to change considerably. Because of this formulating an accurate occupational exposure picture for most workers over time is currently not possible. The fact that occupational histories of workers is generally poorly documented is a source of numerous occupational lawsuits, not only in the United States but worldwide.

The technology described here would help overcome these difficulties and allow the accurate measure of cumulative exposures as well as real time monitoring of workers for any hazard throughout their careers. It is therefore a universal exposure monitor.

The present invention is possible in light of recent advances in micro-electronics, communication technologies and micro-sensor developments. It specifically discloses a novel method to integrate some of these advances into a new type of monitor.

In one aspect, the present invention provides a small wearable worker-specific device comprising at least one central low-power microprocessor with a data storage capability, a built-in power source and a built-in slot to house a removable exposure module.

In another aspect a self-contained exposure module is provided which can be directly inserted into the worker-specific monitor. The exposure module is specifically manufactured to work in conjunction with the monitor and comprises all the features to make the hazard(s) self-identified and coded, including at least one memory for critical exposure limits storage, at least one built-in sensor (or alternatively a nanosensor array chip) and a single interface for power and data upload/download. The nanosensor array can be specifically built to match exactly industry-specific combination of hazards or even the putative genetic susceptibilities of a given individual with his work environment and his/her likelihood to be exposed to given chemicals or given mixtures of hazards.

In another aspect a geolocation system is provided which allows position data to be precisely correlated with exposure or environmental monitoring data. Via a two-way communication link, the exposure data can be requested from the monitor unit for real-time monitoring with geolocating by the host system. Such communication can also automatically be activated if a worker enters a sensitive area or is suddenly exposed to a high level of a toxic element so that other workers can be positioned and immediately notified about a hazardous condition at the site.

In another aspect a convenient recharge/download feature is provided which allows the monitor to be easily recharged and at the same time send/receive data to and from a central monitoring station.

Thus, it is an objective of the present invention to provide a convenient and fully automated method for the collection of exposure data for workers throughout their life by the use of a universal monitor and to allow individuals to custom-tailor their own monitor according to their given concerns, their job environments and their known or potential medical and genetic susceptibilities. The monitor is specifically designed to be either used in a household setting and allow self-monitoring or be used in an industrial setting with the control of the information belonging to the worker, his union and/or the site medical department.

It is a further objective of the present invention to provide a method to survey not only the occupational exposure of single workers but of an entire workforce in a large industrial complex.

Finally the present invention provides a highly sensitive and innovative method to provide security for workers in sensitive jobs through a security tag combining positional and detection capability for any type of chemical or specific mixture of chemicals.

DETAILED DESCRIPTION OF THE PREFERRED EMBODIMENTS

The following detailed description is organized into individual discussions of the several components that comprises the personal monitor system of this invention. The personal monitor itself has several subsystems, including the monitor housing with its various controls and input/output links, the individualized sensors that plug into the monitor housing, geolocating capabilities (GPS or the radar-responsive tags), and the on-board computing capabilities of the monitor. The complete system also includes base stations for reading out data from the personal monitors, for recharging the monitors, and antennae for use in the geolocation of the monitors.

Monitor Configuration

Figure 1A:
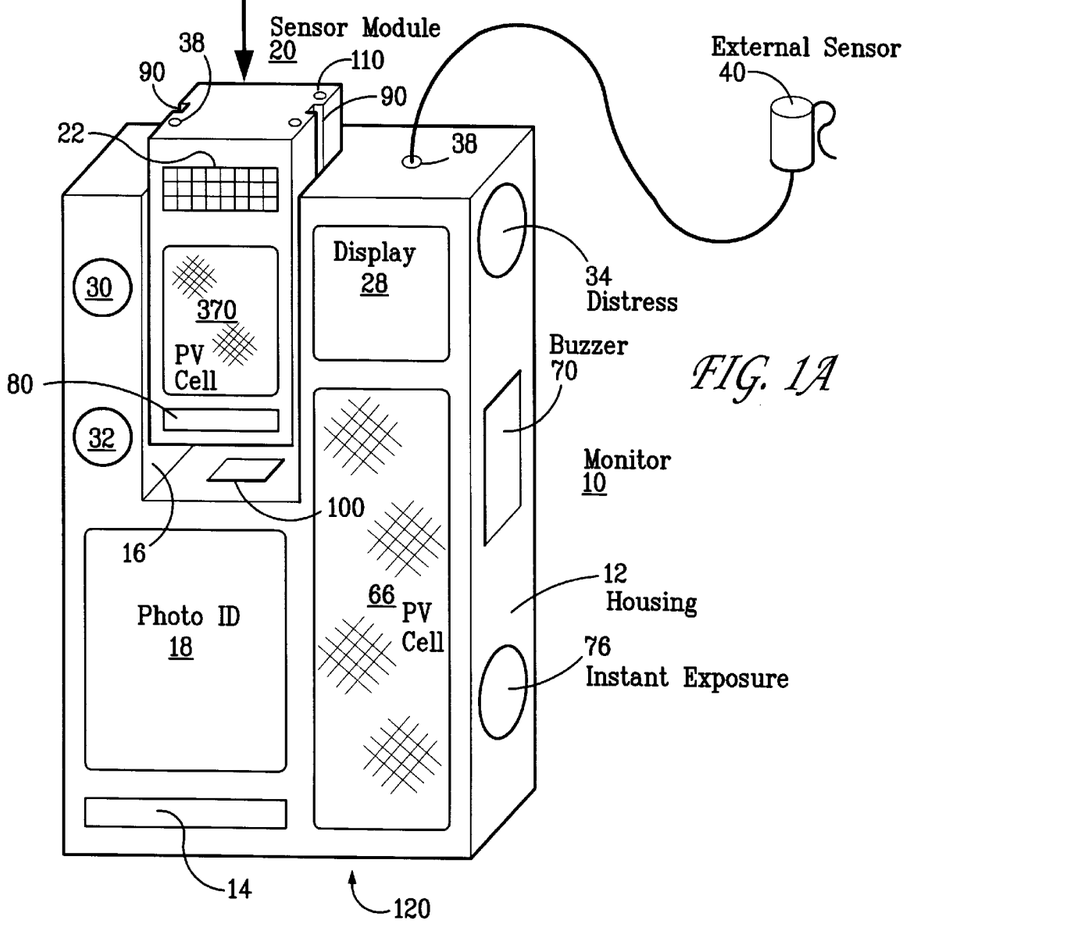
FIGS. 1A and 1B are a side elevational drawing of the monitor with the sensor module and the recharge/transmission console.
Figure 1B:
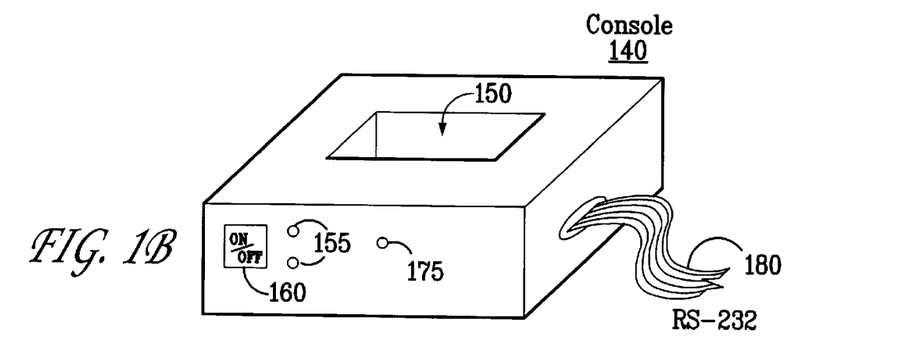

Referring now to FIG. 1 of the drawings, the electronic monitor 10 comprises a housing 12 with a built-in slot 16 to house a removable sensor module 20. Grooves 90 in the sensor module 20 align with protrusions, not shown, in the monitor 10 to guide the sensor module 20 into the slot 16. Monitor 10 has a unique electronic signature which make it and its data worker-specific. The internal electronic signature may match an external code such as a bar code 14. An optional photo ID slot 18 may also be included to allow external identification of the owner and allow the monitor to serve as a ID card. Only the worker or his designee (such as a labor union or the medical and personnel departments) have access to the worker-specific internal code(s) which permits decryption of the monitoring data.

Monitor 10 includes a Liquid Crystal (LC) display 28 to give an instant readout of the exposure(s) and other key monitor features, including on/off status, battery status, time, sensor status, minutes between exposure readings, cumulative exposure values, two way communication on/off, low power mode and interpretation of warning signals (low battery, restricted area, overexposure, sensor non-match area and data storage full).

Monitor 10 includes a rubber sealed multi-function button 30 and a rubber sealed confirm button 32 with a time sensitive confirm function. These buttons allow the user to set the following functions: turn monitor on/off, reset overexposure warning, activate two-way communication, set time between exposure readings, set clock time, set monitor in low power mode, and activate only specific sensors (see below). Monitor 10 can include at least one built-in jack 38 to plug in an external sensor 40. Monitor 10 includes a recess, not shown, to house either a disposable or rechargeable battery such as a Lithium (Li) ion battery.

Monitor 10 includes a convenient attachment system such as a clip-on hook (not shown) or a housing pouch (not shown). Monitor 10 includes an optional high power photovoltaic cell 66 to help reduce the power drainage on the battery. Monitor 10 includes an overexposure buzzer 70 for the instant notification of an overexposure and/or that the worker is using the wrong type of exposure module, given his location in the industrial complex. Furthermore each monitor warns the user about cumulative overexposures and has a reset function. The data for cumulative overexposure are calculated and transmitted from a remote computer storing the records (see below).

Monitor 10 includes a built-in space (not shown) to receive an optional positional two-way microwave/communication card receiving input from external positional interrogators. When this optional feature is used, positional data are merged with the worker-specific exposure data. This technology allows exposures to be pinpointed across an entire industrial complex. The data can also be used to instantly warn other workers at potential risk in case an overexposure has occurred at a given site location for one of the workers. Furthermore the signals from the positional beacons may be used to warn a worker that he/she is wearing the wrong type of exposure module for a given location in an industrial complex or that he/she is entering a restricted area. Finally being able to position precisely the location of each worker combined with a sensing capability for any given chemical make this device an ideal security badge.

Monitor 10 can house in lieu of the optional positional two-way communication/positional card a telemetric card to directly transmit/receive the data to a central computer. The telemetric feature may be spread-spectrum radio signals.

Monitor 10 can be set to override the built-in values for exposure monitoring (typically set at 5 minutes) using alternative set values such as 1 min, 2 mins, 5 mins, 10 mins, etc. or by pressing an external button 76 for an instant exposure readout. The monitor may also be set to work in "low power" mode where all of its principal features are only activated upon activation of the sensor. This feature is particularly attractive when a nanosensor array is used (see below) and only one or a few of the principal micro-sensors are selectively activated by setting the monitor in low power mode. Selection of specific micro-sensors may be either programmed in the sensor module memory (see below) or through the multi-function button. In low power mode no exposure readings are taken until one or several of the selected micro-sensors are activated. Data would be clock-correlated and indicate "no exposure". In this mode the power requirements may be so low that the energy from the photovoltaic cell(s) may be sufficient to maintain indefinitely the monitor in that stage.

Removable Sensor Module

In a preferred embodiment, sensor module 20 is removable and is built to minimize power consumption and maximize reliability and features. Several types of sensors could be included in the module. An example is a nanosensor array (sensor array on a chip) which would allow the inclusion of multiple different sensors in a very small area while having very low power requirements. Sensor module 20 is specific for a given hazard or combination of hazards which is defined by a coded external label 80. Sensor modules can be customized to measure specific mixtures of chemicals for which an individual may have a unique sensitivity or predisposition (as determined by medical and/or genetic tests).

Sensor module 20 may comprise a nanosensor array, other types of advanced micro-sensors, or alternatively at least one built-in conventional sensor. It would include at least one air intake grid 22, protecting the sensor(s) or nanosensor tips. Nanosensor tips are typically coated with materials allowing chemical-specific reactions (such as gold and mercury).

Sensor module 20 can be specifically built to detect typical occupational hazards or combinations of occupational hazards including heat, humidity, noise, particles, radiation, given chemicals, etc. Past personal monitors typically could detect only a single hazard. Industry specific modules may also be built which would encompass the most commonly encountered occupational hazards of a given industry. Examples of advanced sensors that can be built as an array include surface acoustic wave and quartz crystal microbalance sensors that are responsive to the mass of a specific chemical or class of chemicals present upon the resonating surface of the sensor element.

Sensor module 20 may include an automatic reset feature which can be activated on the spot, particularly if a nanosensor array is used and if there is an overexposure. Depending on the hazard, this reset feature can be as simple as briefly heating the coated tip of the micro-sensor to a set temperature to clear the micro-sensor tip of the given contaminant. In the case of larger sensors where power requirements may be a concern, this reset feature may take place only when the monitor is being recharged. It is indeed assumed that a worker would exit the hazard area following an exposure and return his monitor to a recharge/transmission console (see below) which typically would be located in the changing area. If a given sensor needs replacement or recalibration, a warning signal may be sent to the central monitoring station.

Depending on the type of hazard, each sensor module 20 has a plug-in capability 38 for at least one external sensor 40. The purpose of this feature is to allow readings to be taken as close as possible to the face or the target exposure organ for specific types of exposures where such readings may be more accurate. If an external sensor or micro-sensor is used it overrides the build-in sensor. Furthermore a code is provided indicating that the data reflect external sensor readings.

Sensor module 20 may also include an optional high power photovoltaic cell 370. The purpose of this cell is to provide power in the low power mode and help recharge the battery. Sensor module 20 slips into the monitor via a convenient attachment mechanism which includes grooves 90, a connection port 100 for power and data transmission and a lock-in button, not shown.

Sensor module 20 includes a self-test electronic feature which can trigger an external cue (such as an optional green/red LED 110) and/or a warning on the LC display or the beeper, indicating potential problems with the sensor. In addition to its built-in self calibration and self-testing features, each sensor module 20 can be easily recalibrated/tested either at the factory or through a calibration kit.

Contrary to problems with some conventional sensors, problems with micro-sensors and in particular a nanosensor array are expected to be minimized. Furthermore the design of this monitor ensures easy and convenient sensor module replacement.

Recharge/Data Download Console

In its simplest form, both the battery recharge and the download/transmission of accumulated data can be accomplished via a single cable combining a low voltage power line (for example connected to a plug-in transformer) and a computer line (modified RS232). This cable plugs directly into the monitor into an electrical interface port 120, located on the bottom of the monitor 10. Such a setting could be used for single household applications or small factory applications with a few workers. For more complex sites, a convenient system is provided to allow the easy transfer of the data to a central computer. For example a recharge/transmission console 140 at a base station can be provided where the monitor is simply inserted at the end of each shift and the data are automatically transmitted to a remote computer (not shown) while the monitor is recharged. Console 140, which may be programmable via a keyboard, may include at least one slot 150 to receive an individual monitor including connectors for receiving/transmitting data and for supplying power to recharge the Li battery pack of the monitor. Console 140 may include at least one LED 155 indicating working status and an on/off switch 160. Console 140 may also include up to four green/red LEDs indicating exposure status and corresponding to exposures during the past 24 hours, past week, past month and past year.

Console 140 may include an exposure reset button 175 in communication with the exposure reset system on the monitor. Console 140 also includes a power supply 180 and a built-in means for transmitting/receiving data to a remote computer. Transmission may be achieved either through the power line, a phone line, an individual cable (such as an RS232 cable), a network line, or be telemetric.

The data download from the monitor may be a two-step process, where it is first transferred to local memory in the console. This would allow automated download of data to the centralized system via phone modem interface (or other) to be performed on a convenient schedule in order to handle large number of workers. The downloading of data could be programmed as the work environment dictates. In applications where the geolocating/real-time data transfer option is not implemented (see below), the base unit could be located near the work place exit and the download of data and analysis could be performed as the worker leaves his work place to allow for timely medical intervention or other important action.

If a nanosensor array is used, the power requirements may be so low that the monitor may only need to upload data/recharge on occasion (for example once a month) as indicated on the LC display. If the monitor is in low power mode (and no data are collected because no exposure is taking place), the monitor may require recharging or battery replacement and checking only once or twice a year. In this case, the use of disposable batteries may be preferred.

External Computer/Base Station

Since the monitor is meant for long-term data collection (i.e. greater than 10 days or so), the cumulative data are usually meant to be recorded on an external computer system with an associated database. In its simplest form the data can be loaded into a PC as described above. In more complex settings, the records may be stored either by the Labor Unions or the medical department at the sites. The following scenarios are envisioned:

Union or Medical Department computer

For large sites, exposure records would be maintained in a secure computer by the Labor Unions or the site medical department. The computer would include software to decrypt the worker-specific data and automatically update the exposure records of individual workers each time the monitor is returned to the console or the data are sent telemetrically. When data are received, the software calculates cumulative exposures not only over the past 24 hours but over the entire work history, interprets the exposure patterns according to pre-recorded standards, and sends a worker-specific warning signal back to the console and/or the monitor in case of an overexposure. Should an overexposure occur in one area of the plant, the other workers potentially at risk are automatically notified and so is the Labor Union representative and/or the plant manager. This notification can be done instantly if the monitor is equipped with a two-way communication feature as described below or the next day via the console.

Personnel Department

A part of the data from the medical department may be used to indicate time on the job. Indeed the minute a worker picks up his monitor from the console or the minute the worker turns his monitor on can serve as time stamp for when the worker starts his job. When the monitor is returned to the console this would indicate the time the worker ends his shift.

Security Office

The positional capability combined with the flexibility of adapting the device to monitor for any given chemical (or combination of chemicals) allows this monitor to also serve as a highly sensitive security device. If the monitor is used as a security badge, a security monitoring station can be set up to monitor the whereabouts of each given worker combined with real-time monitoring for specific chemicals. Should a worker enter a restricted area as indicated by both his position and given chemical external cues, a warning signal could be sent to the worker or appropriate security measures triggered. In case the monitor is used as a permanent security badge, it may be modified to include more battery power and an inability by the user to turn some features off (such as the positioning feature). Furthermore the monitor may include an accelerometer (not shown) and other similar electronic features to ensure that the monitor is being worn.

Geolocating and Two-Way Communication Capability

In another preferred embodiment, an optional positional feature is provided for large sites with potential complex exposures. The positional capability places only minor additional space and power requirements on the monitor since they can fit on a credit-card size circuit which can be conveniently inserted into the monitor (for example by removing the back cover).

Geolocating functionality will only slightly impact the size of the monitor unit due to the unique geolocating system architecture implemented in the monitoring unit. This is because the sophisticated signal processing is put in the external interrogation system and not the tagging device which means less electronics in the monitor unit itself. This approach permits low cost tags which is of great importance when providing monitoring units for large number of workers. Furthermore, as compared to locating systems such as GPS, which performs elaborate signal processing in the local unit, much less power is required which means smaller batteries are needed. This lowers both the weight and the size of the unit. However, in situations where line-of-sight to 4 GPS satellites can be guaranteed and greater size and weight are acceptable, GPS can be utilized for geolocating. With GPS locating, reduced cost in the locating infrastructure is realized. When reduced weight and size are important and when geolocating in buildings is important, a local geolocating infrastructure is required. Although greater cost is required for the infrastructure itself, greatly reduced cost of the tagging units is realized. With this system interrogators that prompt the tag unit for a response are strategically located in the area of interest. With simultaneous reception of the tag transmission, precision geolocating can be performed.

Furthermore, such a system can be optimized for the area of interest to minimize shadowing, multipath phenomenon, and improve accuracy. The interrogator system could be VHF or UHF which permits all-weather, day-or-night locating and can see through common obstacles such as foliage and many buildings. Other portions of the RF spectrum could also be utilized including frequencies in the X and ISM bands. This architecture of prompting the tag unit for a response permits power savings which reduces battery size and weight as compared to conventional beacon systems. An important feature of this architecture, as compared to having the locating operation done at the monitor unit, is that emergency personnel are in control of the locating operation via the infrastructure at the site, hence, they can perform geolocating in real-time for immediate response. For example, if a worker sends an "emergency call for help" with the monitor's emergency call button, then all efforts can be applied to locating the worker for immediate response. Beacon systems don't necessarily have this capability.

In parallel with the geolocating feature is a two-way data link which permits data transfer from/to the site central management system for the worker's monitor. This permits monitoring the ambient environment in which the worker is located in addition to geolocating.

Figure 3:
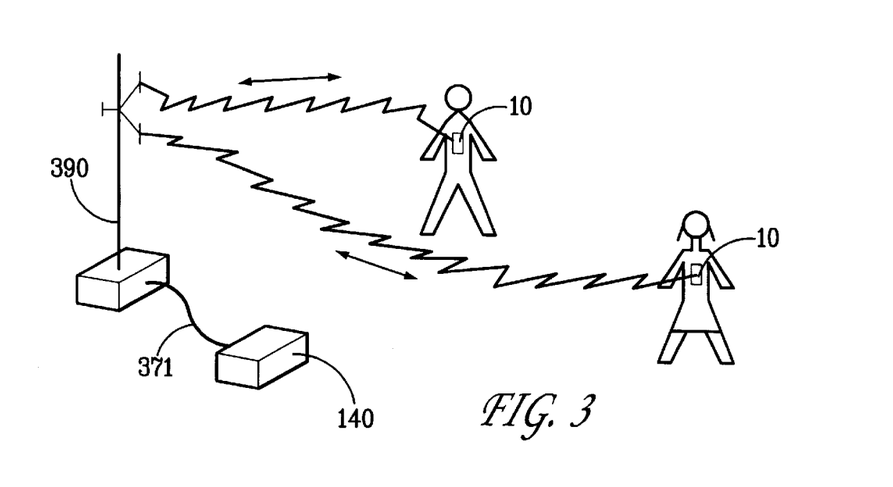
FIG. 3 schematically describes a single antenna interrogator embodiment for the geolocation aspect of this invention.

The UHF (radar) geolocating system may employ a single interrogator antenna or the combination of a single interrogator antenna and two (or more) receiving antennae. FIG. 3 shows a single interrogator 370 with azimuthal angle discrimination by relative phase measurements of incident signals on a three-element, quarter-wavelength spaced antenna array 370. The advantages of single-antenna interrogator systems are reduced cost and less conflict with other systems of other units employing the same geolocating system. Disadvantages include slightly lower accuracy in range measurement and lower resolution in azimuthal angle determination. The geolocation signals and information content travel back and forth directly between the interrogator and the radar-responsive tags in the monitors 10 on the various personnel. The interrogator 370 is connected to the console 140 at the base station by a cable 401.

Figure 4:
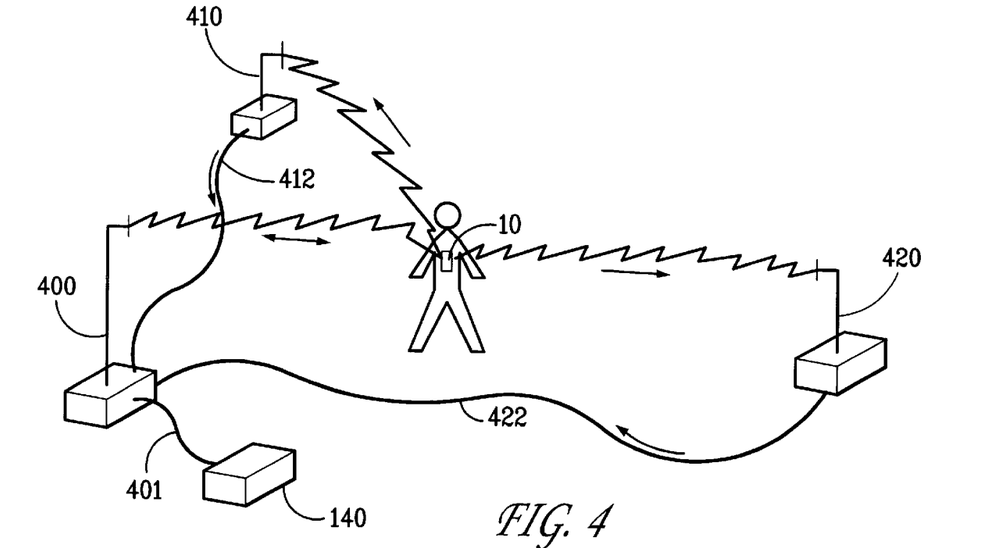
FIG. 4 schematically describes a multiple antenna interrogator embodiment for the geolocation aspect of this invention.

As shown in FIG. 4, the system of the invention may also employ an interrogator antenna 400 and two receiver antennae 410, 420 that are positioned at spacings up to a maximum range (circa 1.5 miles). Such an arrangement produces a large area receiver array that provides processing gain to improve both angle and range resolution as compared to a single interrogator system. Two radar auxiliary receivers 410, 420 with communication links 412, 422 to the single interrogator 400 are required. Auxiliary receivers will be smaller than the interrogator and require lower power. Location of the receivers (and the interrogator) may be performed by reference to a known grid or building plan, by GPS or by incorporating a transponder mode in the auxiliary receiver to respond to a special interrogator prompt. The antennas on both interrogator and receivers are preferably a singe half-wave dipole antenna, which may be telescopic. In this embodiment, the interrogator 400 sends out a locating pulse which interacts with the radar-responsive tag in the monitor 10. The tag then re-radiates with its unique signal which is then received by the various antennae for geolocation of the monitor. Time-of-arrival with a triangulation algorithm is preferably used for tag position determination. The tag will also transmit other information back to the interrogator 400, and the interrogator can also transmit other information directly to the monitor besides the geolocation pulses. The information received from the antennae is then conveyed to the console 140 via cable 401 and to the remote computer.

Advantages of the interrogator/auxiliary receiver combination system include greater range resolution and greater angle resolution. Disadvantages include area of coverage is reduced for a given interrogator power by a factor of approximately four; failed operation of one unit yields system inoperative; and greater conflict with systems of other units.

A hybrid system, not shown, may be employed which exhibits the advantages of both the above systems. The interrogator has a three-element, quarter-wavelength spaced antenna array for both range and coarse azimuthal angle determination. However, it has a second mode of operation in which it operates with auxiliary receivers utilizing a triangulation locating algorithm for higher accuracy when needed.

The spectrum used is preferably UHF, which permits excellent all-weather operation and both foliage and building penetration. This also permits smaller, lighter, and longer life RR-tags than possible with higher-frequency links. The data link may be low energy, spread spectrum.

The present invention provides not only varying the transmit code to/from the RR-tag, but also for correlating to multiple codes at the interrogator unit. With this innovation, one is able to transfer data without increasing the transmission length.

Figure 5A:
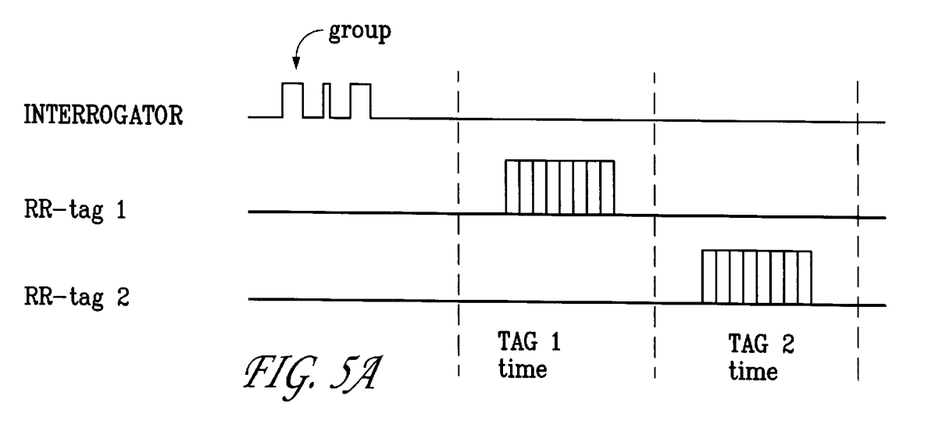
FIGS. 5A, 5B and 5C show three different possible radar pulse exchange cycles between the interrogator at the base station and the radar reflecting tags on the personal monitors.
Figure 5B:
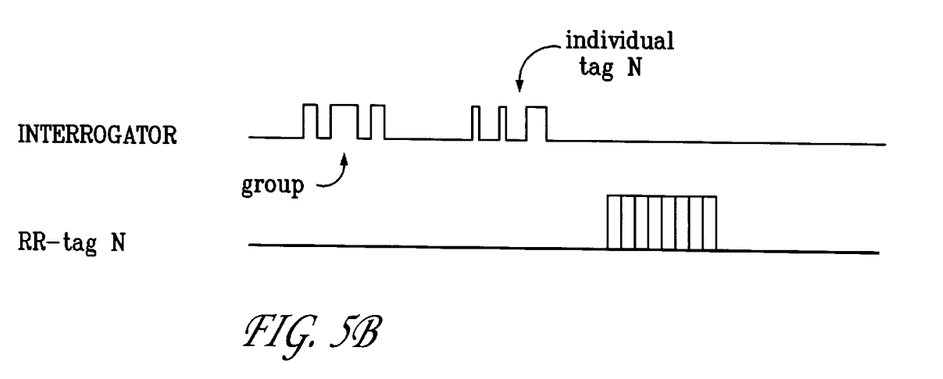
Figure 5C:
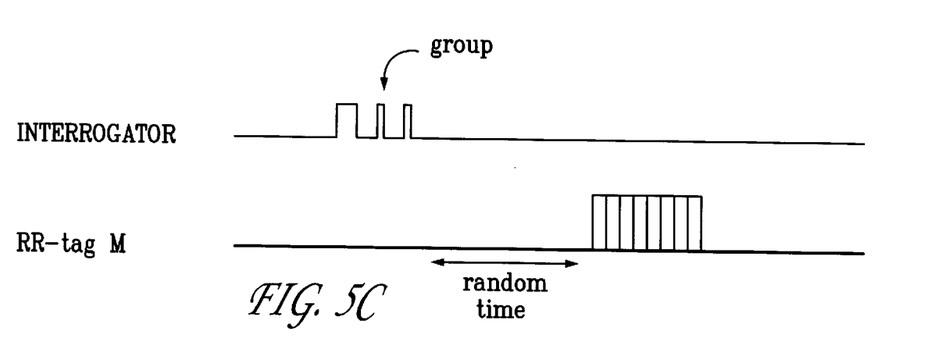

FIGS. 5A, 5B and 5C show three of several possible methods of transmitting and receiving radar pulses between the interrogator and the RR-tags. FIG. 5A shows a method providing the lowest power, but lowest accuracy. The interrogator sends out the radar pulse to the RR-tags that it is responsible for by sending a specific PCM code as shown. The various RR-tags that are programmed to respond to this code respond in assigned time windows as shown. Hence, the particular arrival time of a RR-tag's pulse back to the interrogator will uniquely identify that tag. Additionally, the data contained in the RR-tag's pulsed will be phasecoded to some limited number of bits which convey exposure or other data from the person or object carrying that RR-tag. FIG. 5B shows another method that compromises the interrogator somewhat due to a longer signal pulse, but provides better accuracy in locating the RR-tag. In this method, the interrogator sends out a pulses that alerts all the RR-tags it is responsible for and a second pulse which causes an individual RR-tag to respond. As before, the presence of a response in the allotted time window uniquely identifies that particular RR-tag with the return signal conveying other information in the phase coded modulation of the returning radar signal. FIG. 5C is another variation in which the interrogator sends out a single pulse to all of the RRtags it is responsible for. Each RR-tag has a random generator that controls the time at which it will respond back to the interrogator. The signal for each RR-tag will come back at a different time to the interrogator in almost all cases. Each RR-tag return signal will be a somewhat longer signal than with the previous methods since it will include identification data, the random time delay that RR-tag used (necessary for the interrogator to compute the location of that RR-tag), and additional exposure or other data as well. In all these methods, the range is conventionally computed from the various time delays between the interrogation pulse and the returning RR-tag pulse.

The great benefit in utilizing a radar system for geolocating personnel is that the RR-tag unit on the person is much smaller and exhibits much longer operational lifetime as compared to other technologies including GPS navigators. This is because all the processing work for geolocation is performed by the interrogator and not the unit on the worker. The small form factor and long operational lifetime are an important advantage.

Figure 6:
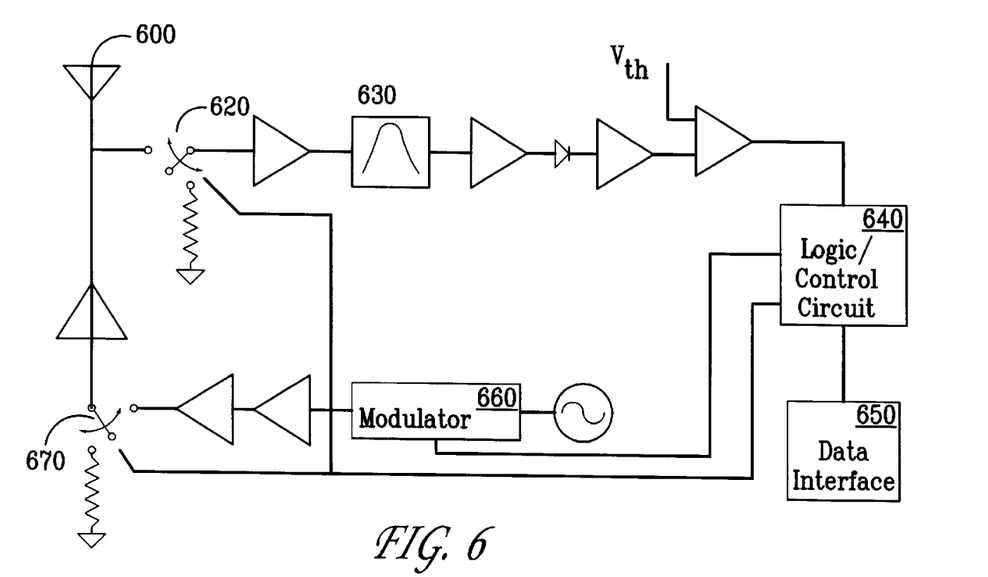
FIG. 6 is a block diagram of one preferred radar-responsive tag.

A block diagram of one embodiment of the RR-tag is shown in FIG. 6. A signal is received from the antenna 600 when the switch 620, under control of the logic/control unit 640, connects the receiving section of the RR-tag in the upper portion of the schematic diagram. The received signal is conducted to the logic/control unit where it will be analyzed to determine if it is the correct signal from the interrogator. If the signal is the correct one, the logic/control unit 640 will then cause the switch 620 to disconnect, the data from the data interface 650 to be modulated by the modulator 660 onto the radar signal it will then transmit after the switch 670 is connected to the antenna 600. Once the transmitted signal is sent, the logic/control unit will then disconnect the transmit switch 670 and reconnect the receive switch 620, and the RR-tag will return to the listening mode. The data transfer function is accomplished by adding a capability of the RR-tag to receive data from the personal monitor. Recall that standard radar systems look for only one code at a time, and hence early tags only transmitted one code. With the present RR-tag, different codes can be transmitted which permits data transfer. This architecture can send large amounts of data and still geolocate the RR-tag.

Figure 7:
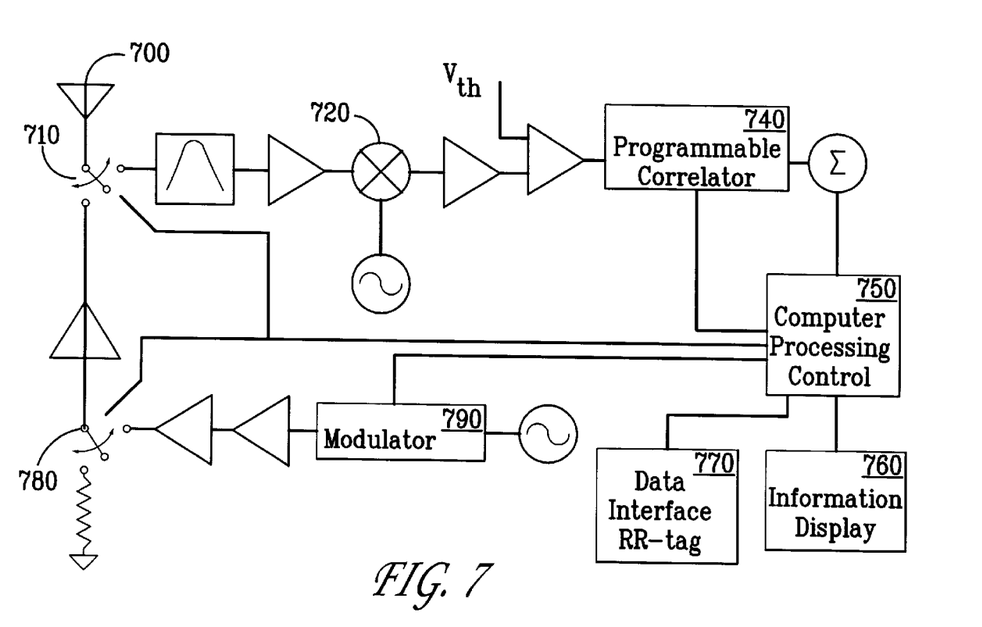
FIG. 7 is a block diagram of one preferred interrogator.

The present invention includes a novel interrogator design as shown in FIG. 7 with significantly more processing power to permit data reception from and simultaneously geolocate the RR-tags. Starting with the transmitting operation, the computer/processing control 750 causes the transmitting switch 780 to be closed and the receive switch 710 to be open. The particular interrogation signal is impressed on the radar pulse by the modulator 790 under the control of the computer/processing control 750. Once this pulse is sent, the interrogator switches to a listening mode with the transmit switch being opened (actually connected to ground as shown) and the receive switch 710 closed. The signals received from the antenna 700 are then filtered, amplified and sent through a mixer 720 to the correlators 740. It should be noted that this figure illustrates the single antenna embodiment for the interrogator. If the single antenna transmit/two antenna receive embodiment were used, the two remote receiving antennas would have data links into the interrogator. The correlators are able to extract the data transmitted from the RR-tags if the codes properly correlate. The received data and the geolocation of the RR-tags are shown to the operator of the interrogator on the information display 760 at the base station. Correlation operations for each possible encoded bit stream should be implemented.

The geolocation system incorporates programmable correlators and parallel correlation operations to receive the data from the tags. This greatly increased signal processing requirements in the interrogator, which is possible with modem high-performance computers. Furthermore, added security is realized by doing the correlation with digital correlators that can be programmed with large sets of codes. By changing the codes periodically, security is insured. The RR-tags can be conveniently re-programmed as well via the data interface 770 to which the individual RR-tags can be connected prior to sending them out to the remote locations.

To reiterate, the single interrogator antenna system can utilize phase measurements or nulling techniques for azimuthal angle determination. To accomplish phase measurements, a small array of antennas spaced one-quarter wavelength apart can be utilized. A minimum of three elements is required in the array. Signals from two of the elements are then mixed to yield relative phase information. All three permutations of elements are measured and combined to determine the angle of incidence. Of course proper multiplexing through filters is necessary to remove filter phase perturbations that would greatly affect the measurements. To utilize nulling techniques, a mechanical or electronically steered antenna (or rotating antenna) is utilized to find the null of the RR-tag signal.

The multiple receiver system can be implemented in a variety of ways. First, the auxiliary receiver could simply send a time stamp of the time-of-arrival of the RR-tag signal at the auxiliary receiver location to the interrogator. In this case, the correlation process is done at the auxiliary receiver. A second implementation uses the auxiliary receiver as a repeater or "bent pipe" that repeats the RR-tag signal at a different frequency or with appropriate delay for subsequent reception by the interrogator. The interrogator then time stamps the signal from each auxiliary receiver. Of course, any delays must be properly accounted for. In this configuration the time-of-arrival at each auxiliary receiver can be calculated the known distance between the interrogator and the auxiliary receivers. With time-of-arrival at each receiver, the RR-tag location is uniquely determined relative to the interrogator.

Precise site-specific positional values can be pre-stored in memory. Furthermore the tag can be remotely activated to go into send/receive mode and allow two-way communication. This is important for example if a worker enters a sensitive area (triggered either by a positional value stored in the non-volatile memory or by activation of the send-receive mode) or if an overexposure is detected for a given worker (so that other workers can be warned). A code corresponding to a message such as "exit the area" and the activation of the beeper can then be sent remotely to selected workers. Furthermore a worker can send a "need help" signal which would be sent together with his position and his identification to the monitoring station. The distress signal would be sent either automatically in case of a high dose exposure or manually by the worker if he requires help by depressing buttons 30 and 32 or through a recessed emergency button 34.

The optional positional feature implies active monitoring of the workforce. This function can either be done by a remote supervisor or software can be provided to automatically warn concerned workers and a given person responsible for monitoring the workers, for example by phone or by beeper via a computer.

Instead of the positional/communication feature a more simple low power telemetric module can be included for the real time monitoring of workers with a two way communication system. This may be particularly useful for specialized settings such as nuclear waste cleanup operations.

Monitor Electronics

Figure 2:
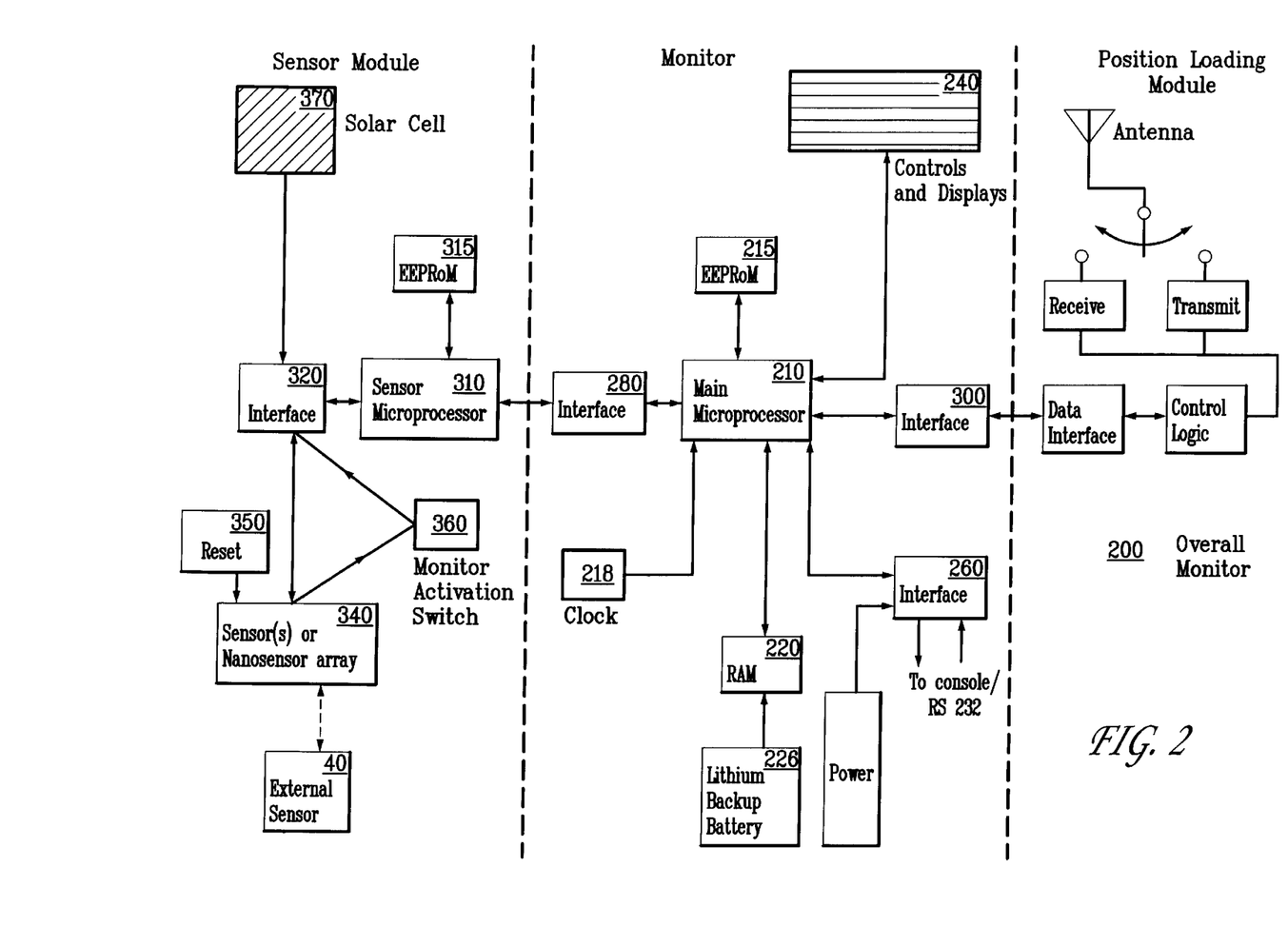
FIG. 2 is a schematic electrical diagram for the monitor including the sensor module and the geolocating system.

Referring now to FIG. 2 of the drawings, the preferred control configuration 200 is shown. The electronic controls for this device can be constructed using standard and widely available components. More specifically a central low-power microprocessor 210 is provided which provides central control for all the features described. Microprocessor 210 includes a programmable memory 215 and a clock 218 both of which may be built-in. Microprocessor 210 encrypts the worker-specific data through a monitor-specific code, permanently programmed in the device. Clock 218 can be remotely reset locally by use of the multi-function button 30 or remotely by radio or microwave signals and its function is to control the timing between the periodic exposure readings. This is to reduce as much as possible power requirements. Precise timing can be particularly important for certain geolocating architectures. Generally the time-stamped exposure data are correlated to the time-stamped position data at the central monitoring site. Overall data storage is in RAM 220, which includes a replaceable Lithium backup battery 226.

Microprocessor 210 is connected to all the controls and displays (including the buzzer 70) as indicated schematically as item 240 and as fully described in the preferred embodiments above. Microprocessor 210 is connected to power interface 260 which has the dual function of providing a connection to the power source (including the photovoltaic cell) and the connection to the download/upload port. Interface 280 allows the connection of the main microprocessor to the sensor module, while interface 300 allows its connection with the optional positional/communication card described in more detail above.

Referring to the sensor module component on the left of FIG. 2, a low power sensor microprocessor 310 is provided. This microprocessor converts the sensor or micro-sensor signals to actual readings with the help of stored data reference points stored in memory 315. Depending on the sensor type an additional sensor interface 320 may be included for signal sharpening/and nanosensor connection.

Microprocessor 310 identifies each specific hazard and ties a hazard-specific code to each of the readings sent to storage in RAM 220. Should any of the readings (or combination of readings) indicate an overexposure, a warning signal is sent to the main microprocessor 210 for processing. The sensor or nanosensor array 340 is fully integrated and may include microplates for micro-sensor tip heating and resetting as controlled by reset function 350. Nanosensor array 340 may have specific codes associated with specific micro-sensors for identification purposes. For example value X may always correspond to micro-sensor X for measuring exposure to external agent X. Nanosensor array 340 may also include a monitor activation switch 360 which sends a "power on" signal to the microprocessor 210 for use in low power mode as described above. Power to maintain the selected nanosensor low power mode may be provided by an optional high power photovoltaic cell 370. A connection is provided for plugging in an external sensor 40. Depending on the nanosensor array, multiple connections may be provided for an external nanosensor array.

We claim:

1. A person-specific monitor of a size to be conveniently worn upon clothing of a person, the monitor comprising:

a microprocessor with associated memory, a power supply, an RF transceiver to convey information between the person and a separate base station, said information from the transceiver including a signal that enables angular and distance determination of the location of the monitor by the base station, and at least one sensor of a radiological, chemical or other toxic agent in the environment surrounding the person, said sensor being operably connected to the microprocessor and removably attached to the monitor, wherein the microprocessor, power supply, RF transceiver, and at least one sensor are electrically connected together.

2. The monitor of claim 1 further including means to download from the monitor information from the at least one sensor to the base station.

3. The monitor of claim 2 wherein the base station includes means to store the downloaded information from the at least one sensor.

4. The monitor of claim 2 wherein the base station is adapted to physically receive the monitor, such adaptation including means to recharge the monitor power supply.

5. The monitor of claim 4 wherein the base station is further adapted to provide means to reset or recalibrate the at least one sensor in the monitor.

6. The monitor of claim 3 further including means to sense that the person is wearing the monitor, said means having a data output connected to the means to download.

7. The monitor of claim 1 further including separate sensor means adapted to be worn on a location on the person that is remote from the monitor with the separate sensor means being electrically connected to the monitor.

8. The monitor of claim 1 wherein the RF transceiver includes means to provide an identifying signal to radio direction finding means associated with the base station.

9. The monitor of claim 1 wherein the at least one sensor is specific to at least one agent that is known to be detrimental to the person on the basis of that person's genetic susceptibility.

10. The monitor of claim 9 wherein the at least one sensor includes a plurality of detectors, each of which is specific to the agents that represent a hazard based on the person's genetic susceptibility.

11. The monitor of claim 1 wherein the at least one sensor includes a plurality of individual detectors, each of which is specific to the particular hazards found in the particular environment in which the person is present.

12. The monitor of claim 1 wherein the at least one sensor is at least one nanosensor comprising chemical microsensor means integrated with a semiconductor integrated circuit, said chemical microsensor means responding to at least one specific chemical in the environment.

13. The monitor of claim 2 wherein the base station is operably connected to remote means to accumulate the information received from the monitor about the specific worker.

14. The monitor of claim 3 wherein the base station is connected to means to correlate the information from the at least one sensor with the information about the location of the worker to produce a record of the location of the worker at the time that worker was exposed to the agent.

15. The monitor of claim 1 wherein the monitor additionally includes audible means to warn the person if the agent that is sensed reaches a hazardous level.

16. The monitor of claim 15 further including means to convey a signal from the means to warn to the base station, said signal causing the location of the person to be determined at that time.

17. The monitor of claim 16 further including second means to convey warning information from the base station to other monitors worn by other persons in vicinity of the person experiencing the hazardous level.

18. The monitor of claim 2 further including distress signal means to convey a distress signal from the person to the base station.

19. A person-specific monitor of a size to be conveniently worn upon clothing of a person, the monitor comprising:

a microprocessor with associated memory and a power supply, first holding means to removably accept at least one sensor of a radiological, chemical or other toxic agent in the environment surrounding the person, said first holding means including means to provide an electrical connection between the sensor means and the microprocessor, an RF transceiver to communicate information with a remote base station, said transceiver being electrically connected to the microprocessor and power supply, and second holding means to removably accept geolocation means, wherein said geolocation means transmits a signal that is useful to determine the location of the person, said second holding means also including means to provide an electrical connection between the sensor means and the microprocessor and the transceiver.

20. The monitor of claim 19 wherein the base station includes means to determine the geolocation of the person as a function of bearing and distance from the base station in conjunction with information from the geolocation means.

* * * * *